US012758743B2

(12) United States Patent
Dixson et al.

(10) Patent No.: US 12,758,743 B2
(45) Date of Patent: Oct. 13, 2026

(54) DEVICES, SYSTEMS, AND METHODS FOR A CATHETER PORT

(71) Applicant: Boston Scientific Scimed Inc., Maple Grove, MN (US)

(72) Inventors: Erin Dixson, Westborough, MA (US); Laura Emily Richards, Westfield, IN (US); Max A Berman, Eliot, ME (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 766 days.

(21) Appl. No.: 18/299,961

(22) Filed: Apr. 13, 2023

(65) Prior Publication Data

US 2023/0330405 A1 Oct. 19, 2023

Related U.S. Application Data

(60) Provisional application No. 63/330,798, filed on Apr. 14, 2022.

(51) Int. Cl.
*A61M 25/00* (2006.01)
*A61M 25/01* (2006.01)
(Continued)

(52) U.S. Cl.
CPC . *A61M 25/0097* (2013.01); *A61M 2025/0188* (2013.01); *A61M 2025/0681* (2013.01);
(Continued)

(58) Field of Classification Search
CPC ...... A61M 25/0097; A61M 2025/0188; A61M 2039/0279
See application file for complete search history.

(56) References Cited

U.S. PATENT DOCUMENTS 5,935,114 A * 8/1999 Jang .................. A61M 25/0169 604/264
8,945,092 B1 2/2015 Call et al.
(Continued)

FOREIGN PATENT DOCUMENTS

JP 2006522657 A 10/2006
JP 2011509718 A 3/2011

OTHER PUBLICATIONS

International Search Report and Written Opinion dated Jul. 28, 2023 for International Application No. PCT/US2023/065706.

*Primary Examiner* — Bradley J Osinski
(74) *Attorney, Agent, or Firm* — Seager, Tufte & Wickhem LLP

(57) ABSTRACT

The present disclosure relates to medical devices for facilitating introducing, removing, and/or exchanging an accessory and/or tool, such as a guidewire. In an embodiment, a catheter port for introducing an accessory may comprise a body comprising a proximal end, a distal end, a longitudinal axis extending therethrough, and a main channel extending along the longitudinal axis along a length of the body. The main channel may be substantially coaxial with a lumen of a catheter. An extension may extend from the body. The extension may comprise an accessory channel extending through the extension. The accessory channel may be in fluid communication with the main channel. The accessory channel may be configured to accept the accessory. A positive stop may be disposed along the accessory channel. The positive stop may be configured to abut a distal end of the accessory.

20 Claims, 14 Drawing Sheets

(51) Int. Cl.
*A61M 25/06* (2006.01)
*A61M 39/02* (2006.01)

(52) U.S. Cl.
CPC ............... *A61M 2039/0258* (2013.01); *A61M 2039/0264* (2013.01); *A61M 2039/0273* (2013.01); *A61M 2039/0279* (2013.01)

(56) References Cited

U.S. PATENT DOCUMENTS

| | | | | |
|---|---|---|---|---|
| 2004/0204629 | A1* | 10/2004 | Knapp ............... | A61B 17/0218 600/156 |
| 2009/0182200 | A1 | 7/2009 | Golden et al. | |
| 2009/0187147 | A1 | 7/2009 | Kurth et al. | |
| 2019/0022354 | A1* | 1/2019 | Khanicheh ........ | A61M 25/0138 |

* cited by examiner

DEVICES, SYSTEMS, AND METHODS FOR A CATHETER PORT

CROSS REFERENCE TO RELATED APPLICATIONS

This application claims the benefit of U.S. Provisional Patent Application Ser. No. 63/330,798 filed on Apr. 14, 2022, the disclosure of which is incorporated herein by reference.

FIELD

The present disclosure relates generally to the field of medical devices. In particular, the present disclosure relates to medical devices for facilitating introducing, removing, and/or exchanging an accessory and/or tool, such as a guidewire into a catheter.

BACKGROUND

In some medical procedures, a catheter may be inserted into a patient with and/or along a guidewire for treatment. The guidewire may be introduced through or along a catheter or other device prior to or during the procedure. Orienting and introducing the guidewire into the device, system, and/or patient may be cumbersome.

Additionally, during the procedure a second catheter or other medical device may be desired, requiring a catheter or other device exchange. An exchange may involve, e.g., removing the first catheter from an endoscope over the guidewire and advancing the second catheter or device over the guidewire to the desired treatment site. In order to maintain a grip on the proximal end of the guidewire or other tool to control the procedure, it may be necessary that the portion of the guidewire that remains outside the patient be longer than the length of the first catheter being removed. Therefore, medical systems suitable for these procedures may require use of excessively long guidewires that may be cumbersome to manipulate, clutter an operating room, and/or may lengthen procedure time to accommodate complicated device exchanges.

Accordingly, a variety of advantageous medical outcomes may be realized by the devices, systems, and methods of the disclosure.

SUMMARY

In an aspect of the disclosure, a catheter port for introducing an accessory may comprise a body comprising a proximal end, a distal end, a longitudinal axis extending therethrough, and a main channel extending along the longitudinal axis along a length of the body. The main channel may be substantially coaxial with a lumen of a catheter. An extension may extend from the body. The extension may comprise an accessory channel extending through the extension. The accessory channel may be in fluid communication with the main channel. The accessory channel may be configured to accept the accessory. A positive stop may be disposed along the accessory channel. The positive stop may be configured to abut a distal end of the accessory. A slit may extend from the distal end of the body to the proximal end of the body. The slit may extend through the extension. The slit may be in fluid communication with the accessory channel.

In the described and other aspects of the present disclosure, the slit may be configured to receive a tool laterally removable from the main channel through the slit and out of the catheter port. The extension may comprise a pair of guides disposed on opposing sides of the slit along the body about the longitudinal axis. The body may comprise a thinned portion along a wall of the main channel. The thinned portion may be disposed along the length of the body opposing the slit such that the body and the pair of guides may comprise an open configuration wherein the pair of guides are positioned away from each other about the thinned portion and may comprise a closed position wherein the pair of guides are positioned towards each other about the thinned portion. The accessory channel may comprise a larger lateral width dimension at a proximal portion and a smaller than a lateral width dimension at a distal portion. A proximal end of the accessory channel may comprise a funnel-shape having a maximum lateral width dimension that is larger than the remainder of the accessory channel. The main channel may further comprise at least one of a distal shoulder configured to abut a distal end of an aperture of the catheter and a proximal shoulder configured to abut a proximal end of the aperture of the catheter. The positive stop may comprise an annular aperture having a diameter that is abuts an outer diameter of the accessory and is large enough to accept a diameter of a tool disposed within the accessory. The extension may comprise at least one concave portion along an outer surface of the extension. The extension may comprise a flap forming a funnel-shape extending along and laterally from the body. The flap may have a larger lateral width dimension of the funnel-shape towards the proximal end than a lateral width dimension of the funnel-shape towards the distal end. The slit may be disposed along a terminal proximal end of the flap. The slit may be disposed laterally along the funnel-shape. The flap may further comprise a thinned portion along a wall of the flap. The thinned portion may extend along the flap where the flap extends laterally from the body.

In an aspect of the disclosure, a catheter port for introducing an accessory may comprise a body comprising a proximal end, a distal end, a longitudinal axis extending therethrough, and a main channel extending along the longitudinal axis along a length of the body. The main channel may be substantially coaxial with a lumen of a catheter. An extension may extend from the body. The extension may comprise an accessory channel extending through the extension. The accessory channel may be in fluid communication with the main channel. The accessory channel may be configured to accept the accessory. A positive stop may be disposed along the accessory channel. The positive stop may comprise an annular aperture having a diameter that abuts an outer diameter of the accessory and is large enough to accept a diameter of a tool disposed within the accessory.

In the described and other aspects of the present disclosure, a slit may extend from the distal end of the body to the proximal end of the body. The slit may extend through the extension and is in fluid communication with the accessory channel. The extension may comprise a pair of guides disposed on opposing sides of the slit along the body about the longitudinal axis. The accessory channel may comprise a larger dimension at a proximal portion and a smaller dimension at a distal portion. The extension may comprise a flap forming a funnel-shape along the body. The flap may have a larger dimension of the funnel-shape towards the proximal end and a smaller dimension of the funnel-shape towards the distal end. The slit may be disposed along a terminal end of the flap. The slit may be disposed laterally along the funnel-shape.

In an aspect of the disclosure, a catheter system may comprise a catheter port. The catheter port may comprise a body. The body may comprise a proximal end, a distal end, a longitudinal axis extending therethrough, and a main channel extending along the longitudinal axis along a length of the body. An extension may extend from the body. The extension may comprise an accessory channel extending through the extension. The accessory channel may be in fluid communication with the main channel. A positive stop may be disposed along the accessory channel. A catheter may be disposed through the main channel. An accessory may be insertable within the accessory channel such that the accessory abuts the positive stop.

In the described and other aspects of the present disclosure, the main channel may comprise a shoulder configured to extend into a lumen of the catheter such that the shoulder abuts an end of a radial aperture of the catheter. The catheter port may comprise a slit extending from the distal end of the body to the proximal end of the body. The slit may extend through the extension. The slit may be in fluid communication with the accessory channel. The extension may comprise a flap forming a funnel-shape along the length of the body with a larger dimension of the funnel towards the proximal end and a smaller dimension of the funnel towards the distal end.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component in each embodiment of the disclosure shown where illustration is not necessary to allow those of skill in the art to understand the disclosure. In the figures.

DETAILED DESCRIPTION

Figure 1A:
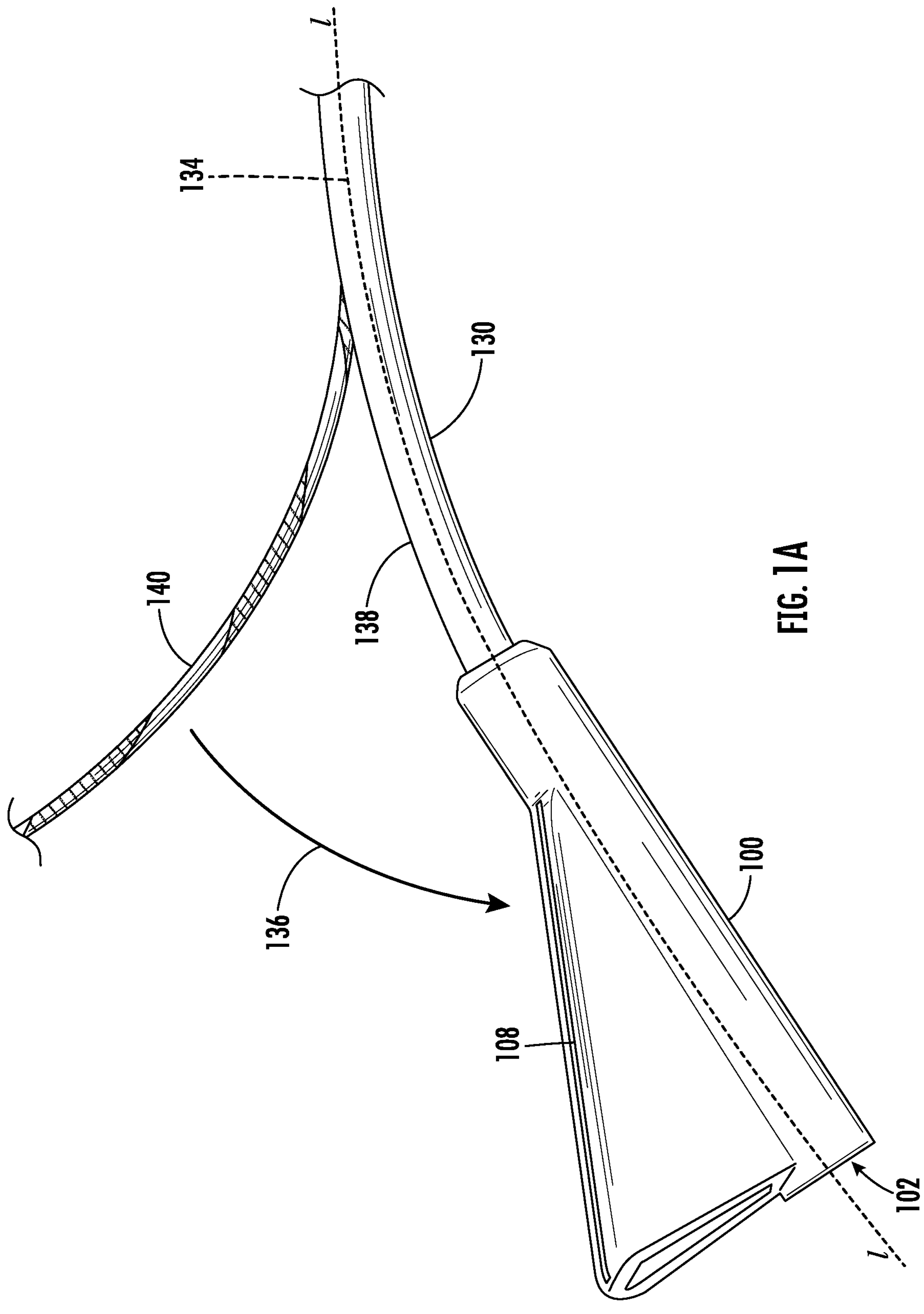
FIG. 1A illustrates a perspective view of a catheter being removed from a guidewire, according to an embodiment of the disclosure.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs. The detailed description should be read with reference to the drawings, which are not necessarily to scale, depict illustrative embodiments, and are not intended to limit the scope of the invention.

As used herein, "proximal end" refers to the end of a device that lies closest to the medical professional along the device when introducing, removing, or exchanging the device within a patient, and "distal end" refers to the end of a device or object that lies furthest from the medical professional along the device during implantation, positioning, or delivery.

As used in this disclosure and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

Although embodiments of the present disclosure are described with specific reference to catheters, guidewires, and funnel accessories, it should be appreciated that other medical devices and/or accessories may be used in a variety of medical procedures. For example, a catheter or guidewire herein may instead be an endoscope, colonoscope, duodenoscope, sheath, working channel of a device, or the like.

Introducing a medical tool, such as a guidewire, into a device, such as a catheter, may be cumbersome because the guidewire may need to enter a lumen of the catheter through a radial aperture (e.g., as illustrated in FIG. 6 and as discussed below) that the guidewire may be misaligned with during introduction. Furthermore, the guidewire may have a shape memory curve (e.g., a J-curve distal end illustrated in FIG. 1B and as discussed below). An embodiment of a port of this disclosure may assist with introducing a guidewire or other tool into a catheter as described herein.

In procedures where a medical professional desires to exchange a first device within a patient for a second device, the medical professional may need to proximally withdraw the first device from the patient over a guidewire until the distal end of the first device is outside the patient. The medical professional may then introduce a second device over the guidewire towards a treatment area in the patient. It may be desirable to exchange the first device for the second device in a more time-efficient manner and/or with less travel distance over the guidewire. To assist with exchanging catheters, the catheters may include "rapid exchange" features. As used herein, "rapid exchange" may refer to any feature of a device (e.g., a catheter, an accessory introducer, or associated parts of a device or system) that reduces the travel distance, time required, or cumbersome tasks to exchange devices within a patient compared to devices without the feature(s). For example, a rapid exchange feature may include an aperture, slot, slit, channel, flap, perforation, weakened area, or the like along a length of the catheter and/or a port configured to allow lateral/radial removal of the catheter from about a guidewire (and/or vice versa: the guidewire removed laterally/radially from about the catheter). To exchange a catheter for another device while maintaining the position of the guidewire in the body, a catheter may be stripped off the guidewire by separating the catheter from the guidewire in a manner such that the guidewire may exit the catheter along the rapid exchange feature (e.g., through a slit or the like). A second catheter or device may then be routed over the guidewire by inserting the proximal end of the guidewire into an aperture of a guidewire lumen, e.g., at a distal end of the second catheter, and distally advanced along the guidewire.

Various procedures may include a guidewire exchange. A guidewire exchange may be desirable when, e.g., a first guidewire is too thick or includes too large a geometric shape to fit through a desired body lumen, or otherwise lacks the desired characteristics. Under such circumstances, a medical professional may leave a catheter substantially in place, withdraw the first guidewire from the catheter, and insert a second guidewire through the catheter to the treatment site. During this procedure, the catheter guides the guidewire to the treatment site. Once the catheter is positioned at a treatment site, it may be desirable to substantially maintain the position of the catheter during the guidewire exchange procedure so that the second guidewire may be guided to the treatment site in a minimum amount of time.

Referring to FIG. 1A, a perspective view of a catheter 130 being removed from a guidewire 140 is illustrated, according to an embodiment of the disclosure. The catheter 130 includes a port 100 along a proximal end of the catheter 130. The port 100 includes a main channel 102 substantially aligned with a longitudinal axis $\ell$ of the catheter 130 and in fluid communication with a lumen 134 of the catheter 130. The catheter 130 is removed from the guidewire 140 by a movement of the catheter 130 away from the guidewire 140 substantially in a direction of an arrow 136, although the guidewire 140 may additionally or instead be moved away from the catheter 130 in a direction substantially opposite of the arrow 136. As the catheter 130 is removed from the guidewire 140, the guidewire 140 radially exits the lumen 134 through a slit 108 of the port 100 and the guidewire radially exits the lumen 134 through a rapid exchange feature 138 (e.g., a slit or other feature as described above) along the catheter 130.

Figure 1B:
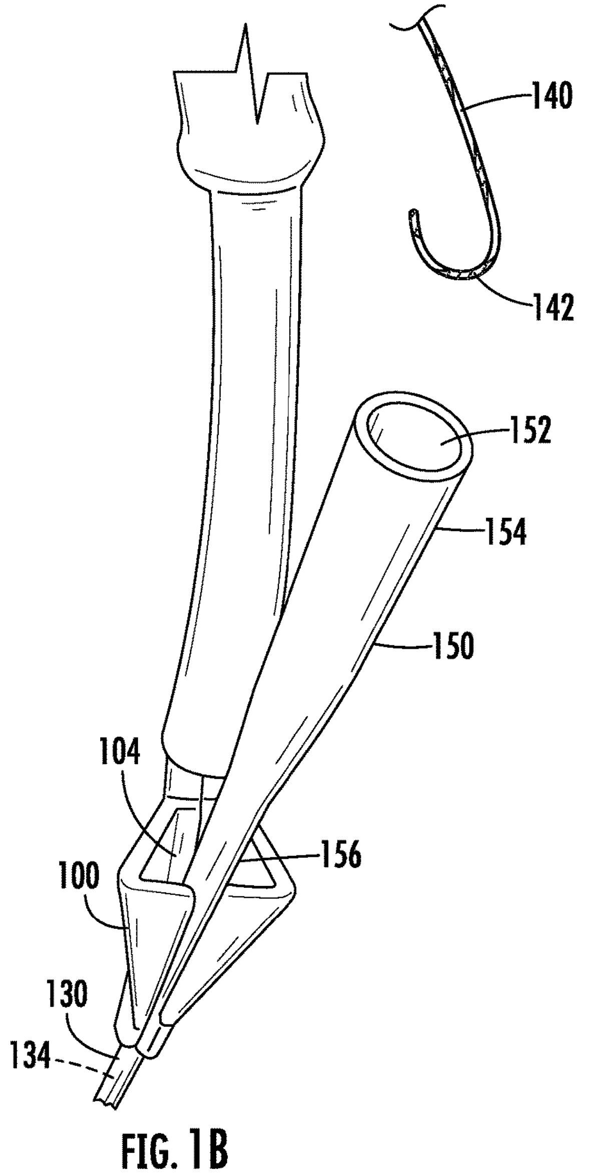
FIG. 1B illustrates a perspective view of a guidewire being introduced into a port of FIG. 1A.

Referring to FIG. 1B, a perspective view of the guidewire 140 being introduced into the catheter 130 of FIG. 1A is illustrated, according to an embodiment of the disclosure. The guidewire 140 includes a distal end 142 having a shape memory J-curve that may be cumbersome to insert into the port 100 and into the lumen 134 of the catheter 130, although any shape guidewire 140 may be employed. An accessory 150 having a funnel-shape is inserted into an accessory channel 104 of the port 100 to assist with guiding the guidewire 140. The accessory 150 includes a lumen 152 through the accessory 150. The lumen 152 has a diameter at a proximal end 154 of the accessory 150 that is wider than a diameter at a distal end 154. The distal end 142 of the guidewire 140 may be introduced into the lumen 152 of the accessory 150. For example, the J-curve of the distal end 142 may be substantially straightened out by hooking the J-curve into the proximal end 154 and distally inserting the guidewire 140 into the accessory 150. As the guidewire 140 is distally translated through the lumen 152, the guidewire 140 transitions along the wider portion of the lumen 152 at the proximal end 154 to the narrower portion of the lumen 152 at the distal end 156. The narrowing transition of the lumen 152 may assist with guiding the guidewire 140 into the accessory channel 104 of the port 100. Continuing distal translation of the guidewire 140 through the accessory channel 104 may advance the guidewire 140 into the lumen 134 of the catheter 130.

Figure 2:
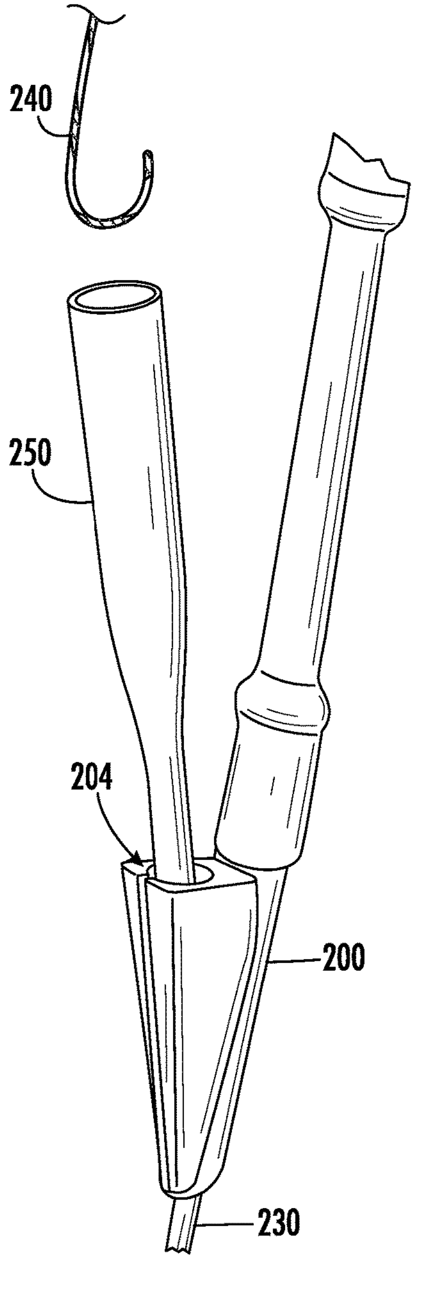
FIG. 2 illustrates a perspective view of a guidewire being introduced into a port, according to an embodiment of the disclosure.

Referring to FIG. 2, a perspective view of a guidewire 240 being introduced into a catheter 230 is illustrated, according to an embodiment of the disclosure. An accessory 250 identical to the accessory 150 of FIG. 1B is inserted into an accessory channel 204 of the port 200 to assist with guiding the guidewire 240. The accessory channel 204 of FIG. 2 has walls formed into inner surfaces complimenting the external surface of the accessory 250. The complimenting inner surfaces of the accessory channel 204 may better support the accessory 250 compared to the accessory channel 104 of FIG. 1B, which is more loosely supporting the accessory 150. For example, the accessory 150 may require assisted manipulation from a medical professional to effectively introduce the guidewire 140 into the accessory 150, whereas the accessory 250 may not require any assisted manipulation from the medical professional to introduce the guidewire 240 into the accessory 250 because of the shaped accessory lumen 204.

Figure 3:
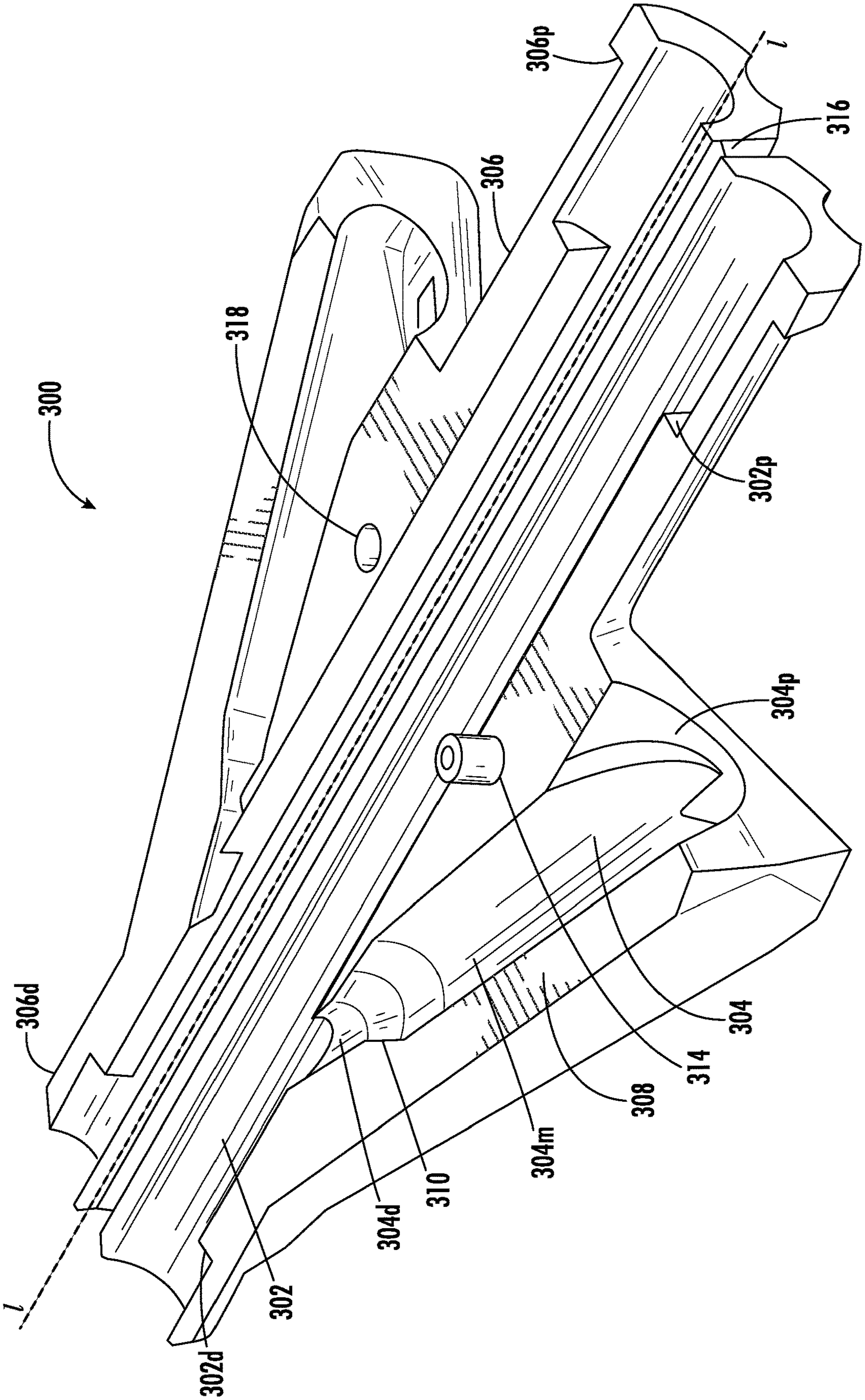
FIG. 3 illustrates a perspective view of a port, according to an embodiment of the disclosure.

Referring to FIG. 3, a perspective view of a port 300 is illustrated, according to an embodiment of the disclosure. The port 300 includes a body 306 comprising a proximal end

306*p*, a distal end 306*d*, and a longitudinal axis ℓ extending therethrough. The port 300 is illustrated in a preassembly open configuration, with the body 306 opened along a hinge 316 extending along the body 306 parallel with the longitudinal axis ℓ. The hinge 316 is a thinned portion of a wall of the body 306. The body 302 can be closed along the hinge 316 such that a main channel 302 is formed extending along the longitudinal axis ℓ that is configured to be coaxial with a lumen of a catheter. A protrusion 314 extends from the body 306 that is configured to couple with an aperture 318 as the port 300 transitions to a closed configuration by closing the body 306 about the hinge 316. An extension 308 extends from the body 306. The extension 308 includes an accessory channel 304 extending through the extension 308. The accessory channel 304 is in fluid communication with the main channel 302 such that the accessory channel 304 may accept an accessory within it and guide the accessory towards the main channel 302. The accessory channel 304 is located along the extension 308 such that the accessory channel 304 meets up with the main channel 302 distal to the protrusion 314 and the aperture 318. The accessory channel 304 includes a positive stop 310 disposed along the accessory channel 304. The positive stop 310 is configured to abut a distal end of an accessory introduced into the accessory lumen 304 such that the accessory is prevented from entering the main channel 302. The accessory lumen 304 includes a proximal portion 304*p* having a maximum lateral width dimension wider than a remainder of the accessory lumen 304, e.g., that may assist with additional space for introducing an accessory into the accessory lumen 304. A midportion 304*m* of the accessory lumen 304 has a diameter smaller than the proximal portion 304*p* that may, e.g., be dimensioned to accept, accommodate, interface with, compliment, friction fit, etc., an accessory. The positive stop 310 has a diameter smaller than the midportion 304*m*. The positive stop 310 transitions from a larger diameter towards the midportion 304*m* and tapers to a smaller diameter towards a distal portion 304*d* of the accessory channel 304. The tapering diameter of the positive stop 310 may assist with ensuring that a distal end of an accessory forms an interference fit with the positive stop 310 as the accessory moves along the tapering diameter of the positive stop 310. The distal portion 304*d* is a conduit for the accessory channel 304 to be in fluid communication with the main channel 302 and may assist with directing a tool at a desirable angle into the main channel 302 and/or a catheter lumen, e.g., towards a direction of the longitudinal axis ℓ. A diameter of the distal portion 304*d* is smaller than that of the midportion 304*m* and may accommodate a tool from an accessory, e.g., such as a guidewire 240 through the accessory 250 of FIG. 2. The main channel 302 includes a proximal shoulder 302*p* and a distal shoulder 302*d*. The shoulders 302*p*, 302*d* may be configured to abut ends of an aperture of a catheter extending through the main channel 302 as described herein.

Figure 4A:
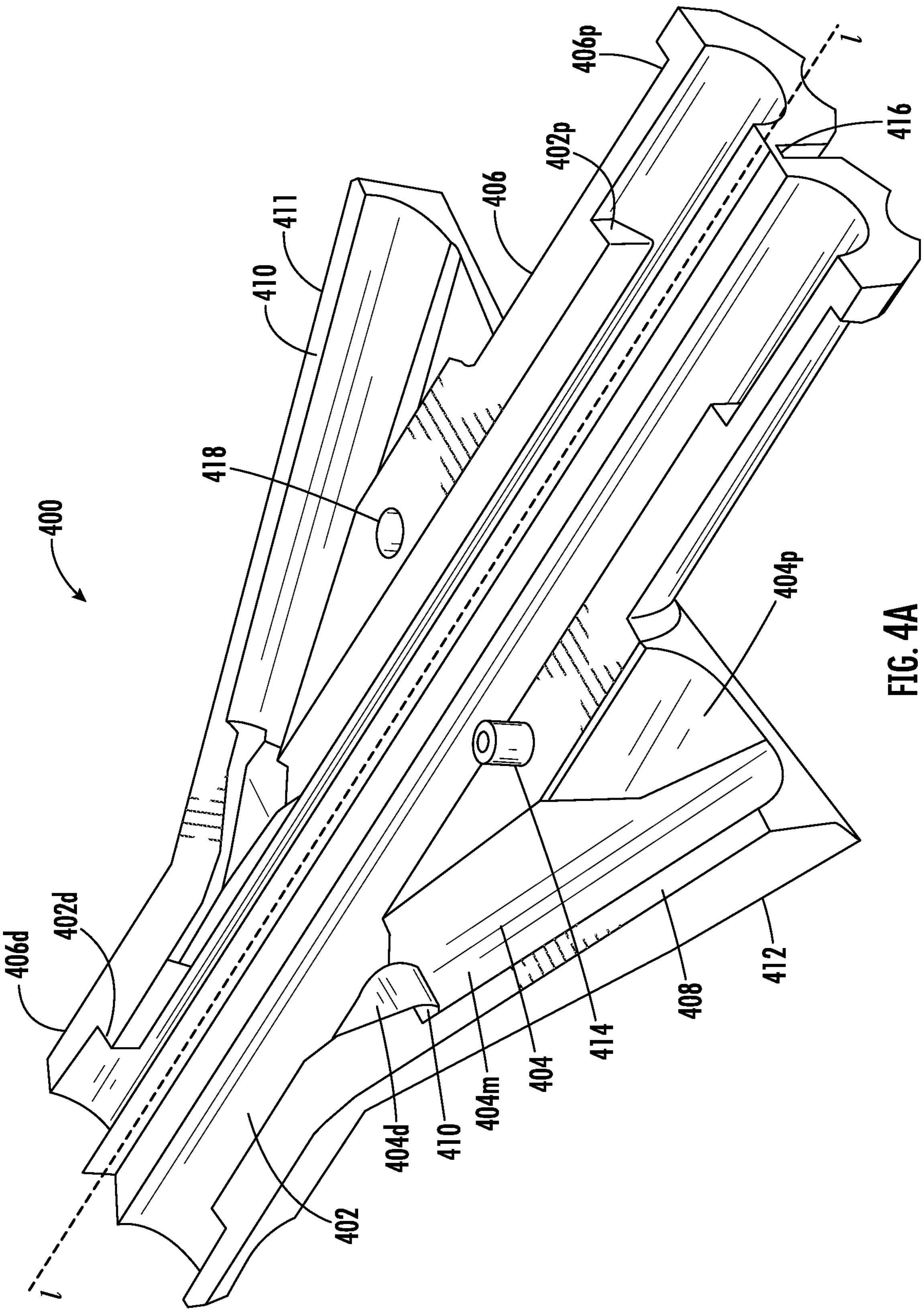
FIG. 4A illustrates a perspective view of a port, according to an embodiment of the disclosure.
Figure 4B:
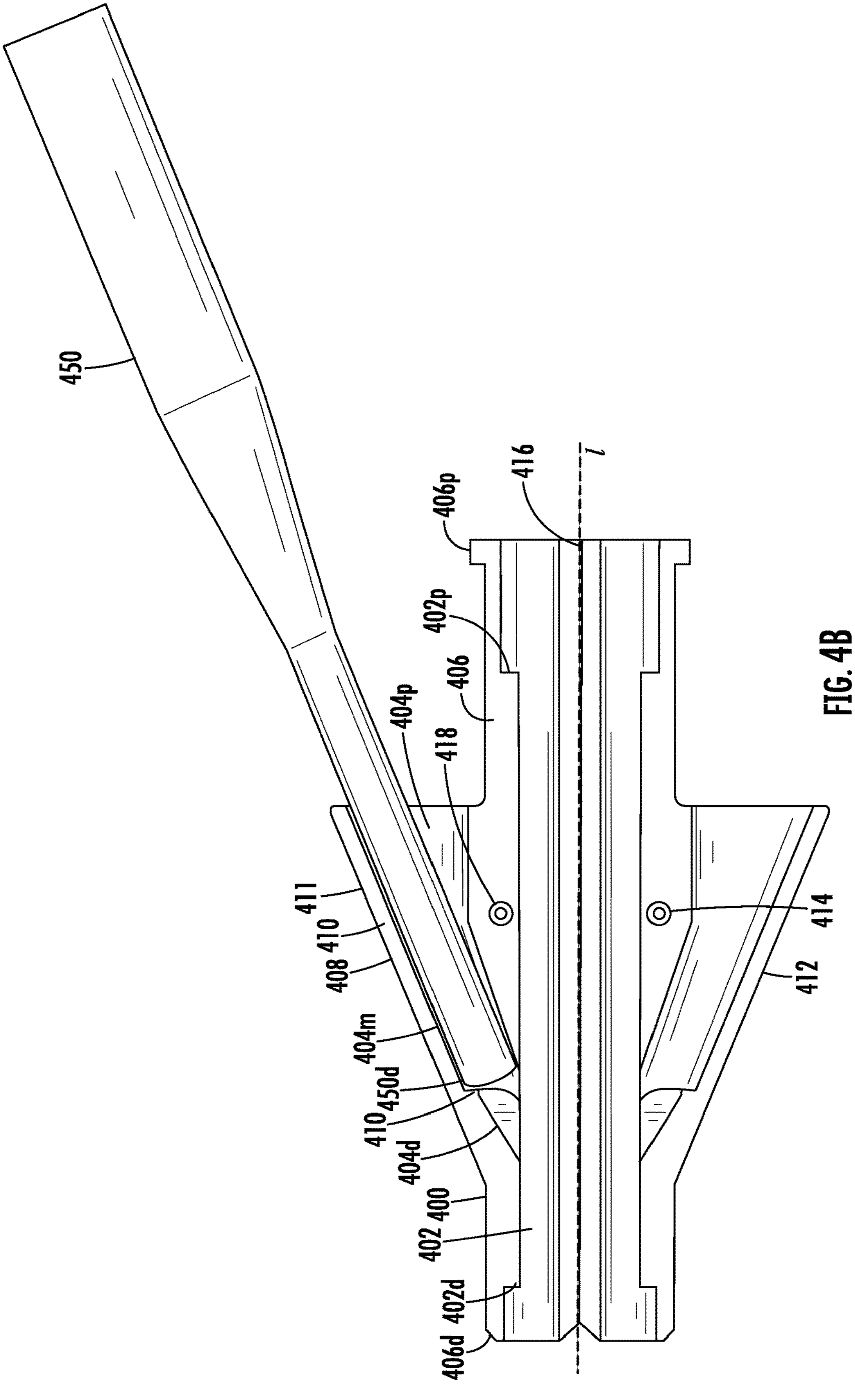
FIG. 4B illustrates a right view of the port of FIG. 4A including an accessory disposed therein.
Figure 4C:
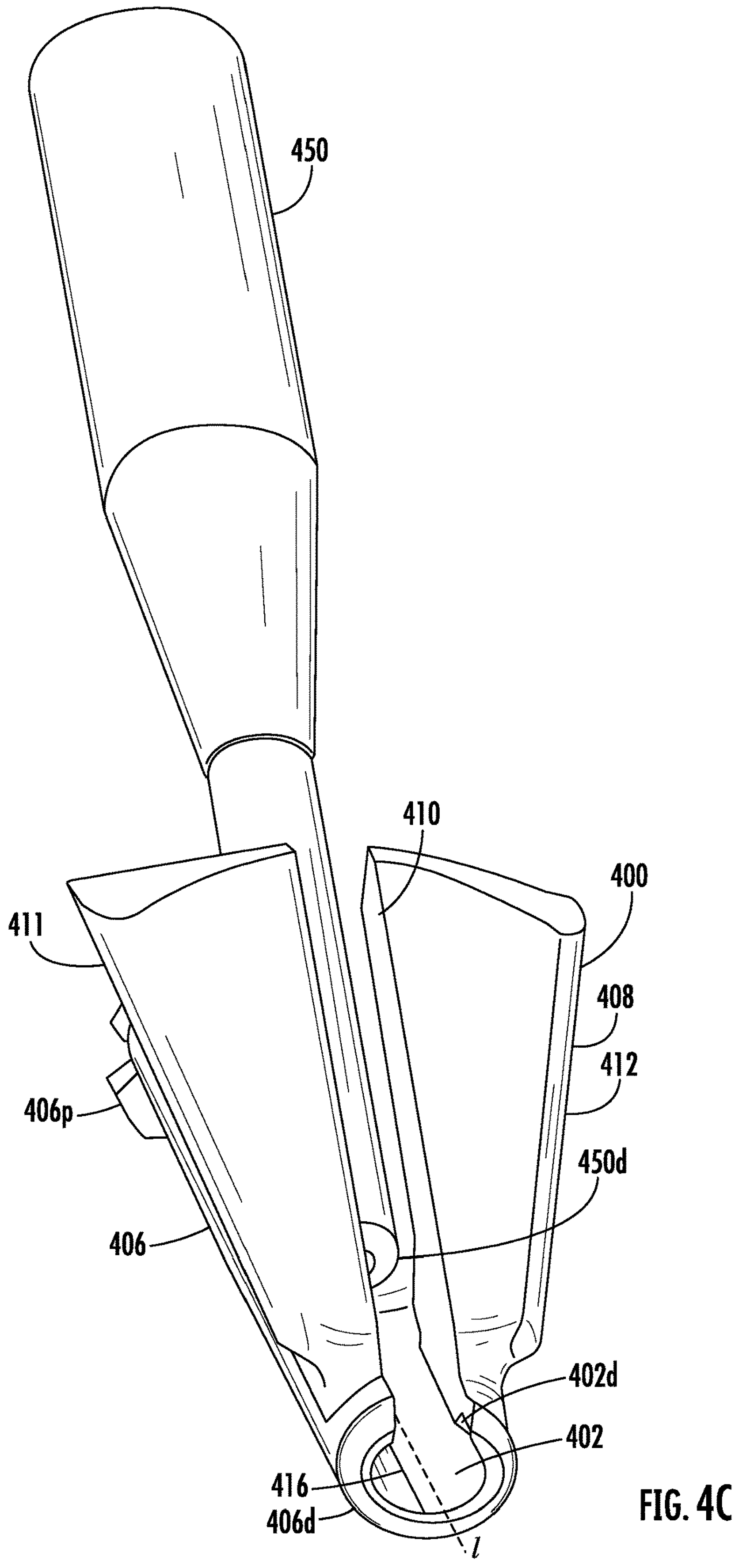
FIG. 4C illustrates a perspective view of the accessory introducer of FIGS. 4A and 4B with the accessory disposed therein.

Referring to FIGS. 4A-4C, perspective and right views of a port 400 are illustrated, according to an embodiment of the disclosure. The port 400 is illustrated in an open configuration in FIGS. 4A and 4B, and in a closed configuration in FIG. 4C. The open and closed configurations of the port 400 are transitionable along a hinge 416, and coupled by a protrusion 414 and an aperture 418, substantially similar to the hinge 316 configuration of FIG. 3. The port 400 includes a body 406 comprising a proximal end 406*p*, a distal end 406*d*, and a longitudinal axis ℓ extending therethrough. A main channel 402 extends along the longitudinal axis ℓ of the body 406 that is configured to be coaxial with a lumen of a catheter. An extension 408 extends from the body 406. The extension 408 includes an accessory channel 404 extending through the extension 408. The accessory channel 404 is in fluid communication with the main channel 402 such that the accessory channel 404 may accept an accessory within it to guide the accessory towards accessing the main channel 402. The accessory channel 404 is located along the extension 408 such that the accessory channel 404 meets up with the main channel 402 distal to the protrusion 414 and the aperture 418. The accessory channel 404 includes a positive stop 410 disposed along the accessory channel 404. The positive stop 410 is configured to abut a distal end 450*d* of an accessory introduced into the accessory lumen 404 such that the accessory is prevented from entering the main channel 402. The accessory lumen 404 includes a proximal portion 404*p* having a lateral width dimension wider than a remainder of the accessory lumen 404, e.g., that may assist with introducing an accessory 450 into the accessory lumen 404. A midportion 404*m* of the accessory lumen 404 has a diameter smaller than the proximal portion 404*p* that may, e.g., be dimensioned to accept, accommodate, interface with, compliment, friction fit, etc., an accessory. The positive stop 410 has a diameter smaller than the midportion 404*m*. A distal portion 404*d* of the accessory channel 404 is a conduit for the accessory channel 404 to be in fluid communication with the main channel 402 and may assist with directing a tool at a desirable angle into the main channel 402 and/or a catheter lumen, e.g., in a direction towards or along the longitudinal axis ℓ. A diameter of the distal portion 404*d* is smaller than that of the midportion 404*m* and may accommodate a tool from the accessory 450, e.g., such as a guidewire 240 of FIG. 2 through the accessory 450. The main channel 402 includes a proximal shoulder 402*p* and a distal shoulder 402*d*. The shoulders 402*p*, 402*d* may be configured to abut ends of a radial aperture of a catheter extending through the main channel 402 as described herein. In the closed configuration, a slit 410 extends through the extension 408, through the accessory channel 404, and into the main channel 402 of the port 400. The slit 410 may be a rapid exchange feature as described herein, e.g., for removing a tool and/or an accessory therethrough. In various embodiments, the slit 410 may be one or more of an aperture, slot, channel, flap, perforation, weakened area, or the like along a length of the port 400. As best illustrated in FIG. 4C, the extension 408 comprises a pair of guides 411, 412 disposed on opposing sides of the slit 410 about the longitudinal axis ℓ. The slit 410 is formed along the extension 408 in the closed configuration opposing the hinge 416. The pair of guides 411, 412 are positioned away from each other about the hinge 416 in the open configuration (e.g., as illustrated in FIGS. 4A and 4B) and towards each other in the closed position.

Figure 5A:
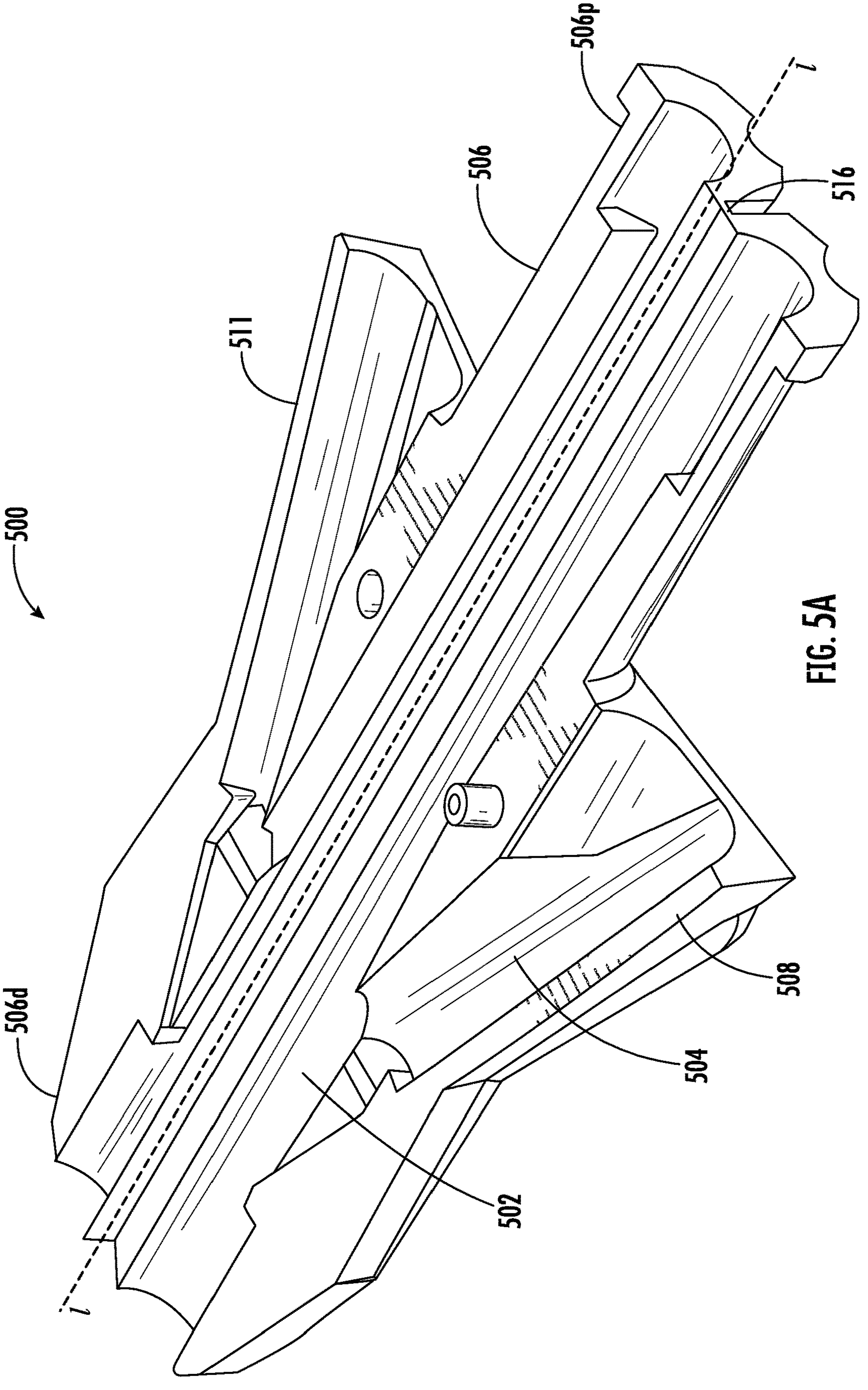
FIG. 5A illustrates a perspective view of a port, according to an embodiment of the disclosure.
Figure 5B:
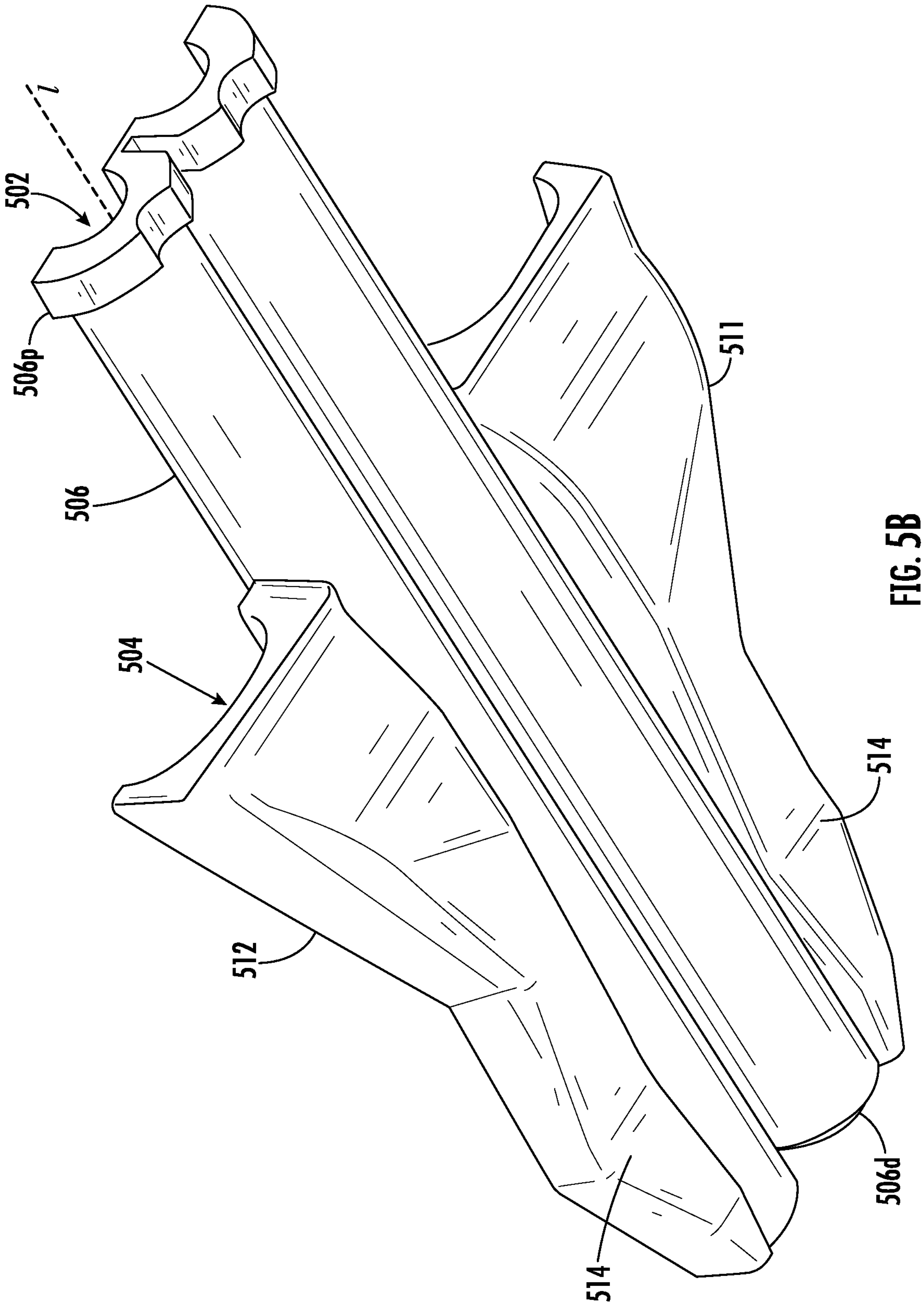
FIG. 5B illustrates another perspective view of the port of FIG. 5A.

Referring to FIGS. 5A and 5B, perspective views of a port 500 are illustrated, according to an embodiment of the disclosure. The port 500 is illustrated in an open configuration transitionable to a closed configuration along a hinge 516, substantially similar to the hinges 316, 416 of FIGS. 3 and 4A-4C. The port 500 includes a body 506 comprising a proximal end 506*p*, a distal end 506*d*, and a longitudinal axis ℓ extending therethrough. A main channel 502 extends along the longitudinal axis ℓ of the body 506 that is configured to be coaxial with a lumen of a catheter. An extension 508 extends from the body 506. The extension 508 includes an accessory channel 504 extending through the extension 508. The accessory channel 504 is in fluid communication with the main channel 502 such that the accessory channel 504 may accept an accessory within it to guide the accessory towards accessing the main channel 502. The extension 508 comprises a pair of guides 511, 512, each having an external surface. The external surfaces of the guides 511, 512 of the extension 508 each include a concave portion 514. The concave portions 514 may assist a user, e.g., a medical professional, with stabilizing, manipulating, and/or assembling the port 500 during or preparing for a procedure by complimenting one or more digits of the user. Additionally, or in the alternative, the concave portions 514 may be pressed towards each other to temporarily close a slit (or other rapid exchange feature), e.g., between the guides 511, 512 when the port is in the closed configuration, for introducing an accessory and/or a tool into the port 500 without prematurely egressing out of the slit.

Figure 6B:
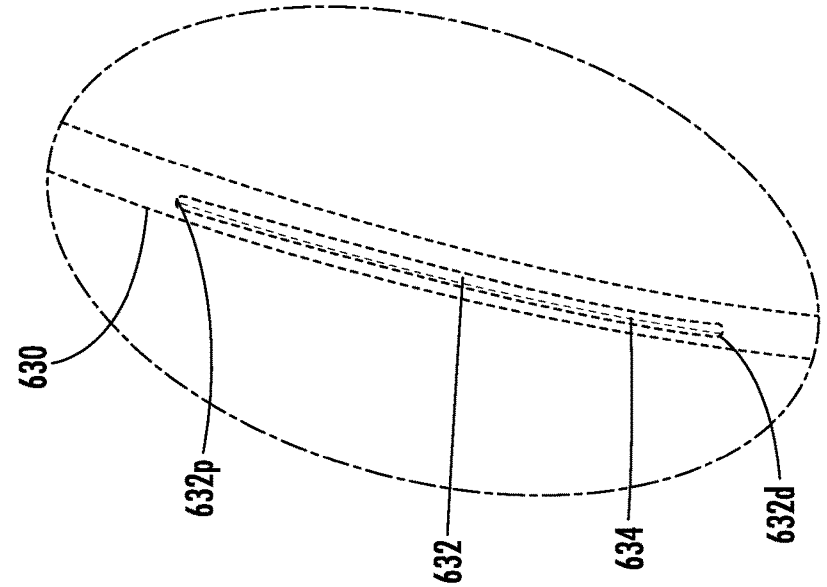
FIG. 6B illustrates a radial aperture of the catheter of FIG. 6A.
Figure 6A:
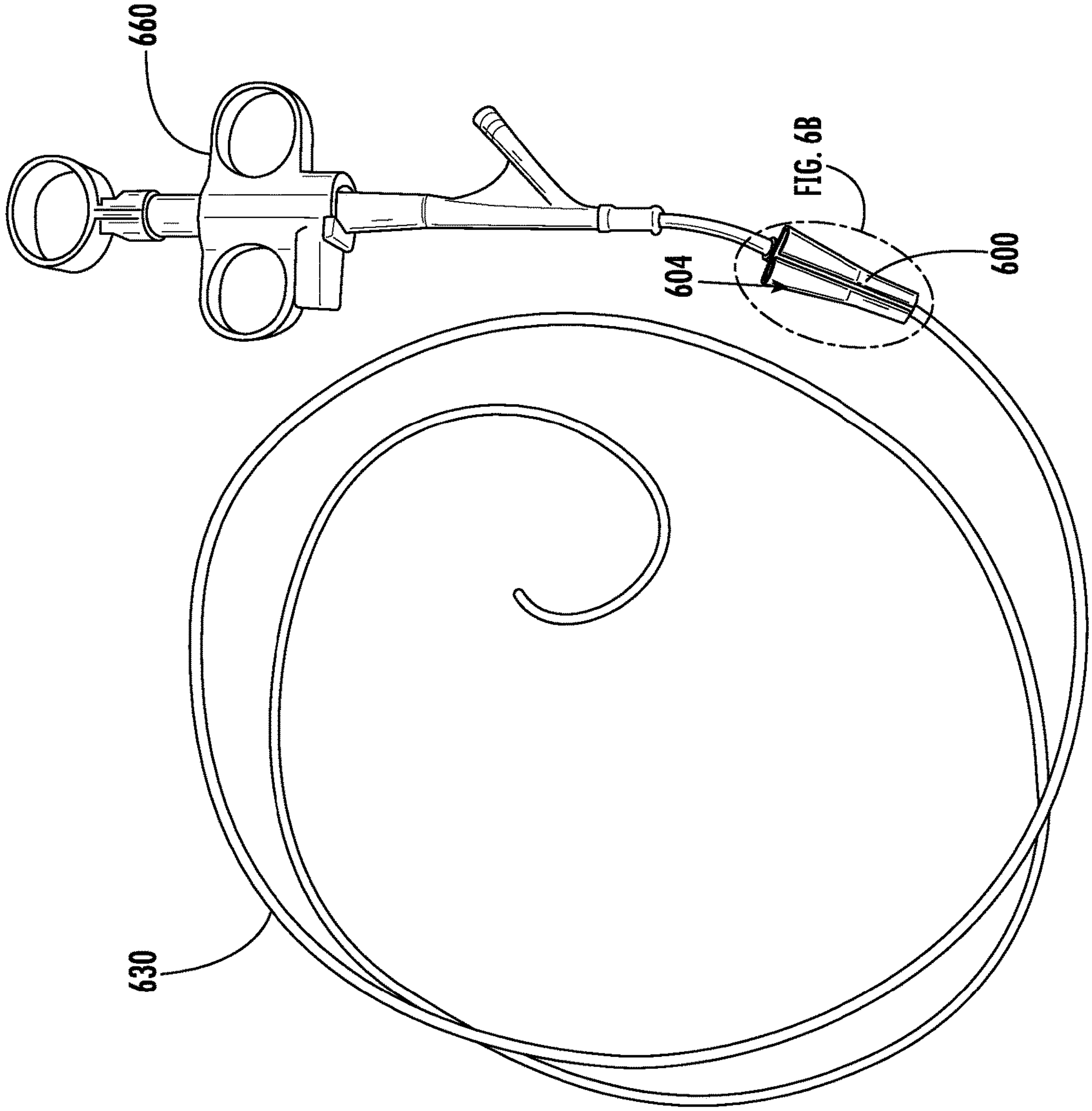
FIG. 6A illustrates a perspective view of a catheter and a port, according to an embodiment of the disclosure.

Referring to FIG. 6A, a perspective view of a catheter 630 and a port 600 are illustrated, according to an embodiment of the disclosure. The catheter 630 is coupled to a handle 660 at a proximal end of the catheter 630. The port 600 is coupled to the catheter 630 such that an accessory channel 604 of the port 600 may allow guided access to a lumen of the catheter 630. Referring also to FIG. 6B, a portion of the catheter 630 is illustrated that is obscured by the port 600 of FIG. 6A. In FIG. 6B, the catheter 630 includes a radial aperture 632 (e.g., a skived cut along the catheter 630) allowing external access into a lumen 634 of the catheter 630. Because the accessory lumen 604 is in fluid communication with the radial aperture 632, a user may introduce an accessory and/or a tool through the accessory channel 640 such that, e.g., the tool may enter the lumen 634 through the radial aperture 632. To ensure alignment, positioning, and/or coupling of the port 600 with the radial aperture 632, one or more shoulders (e.g., shoulders 302*p*, 302*d*, 402*p*, 402*d* of FIGS. 3, 4A, and 4B) may abut one or more of a proximal end 632*p* and/or a distal end 632*d* of the aperture 632.

Figure 7A:
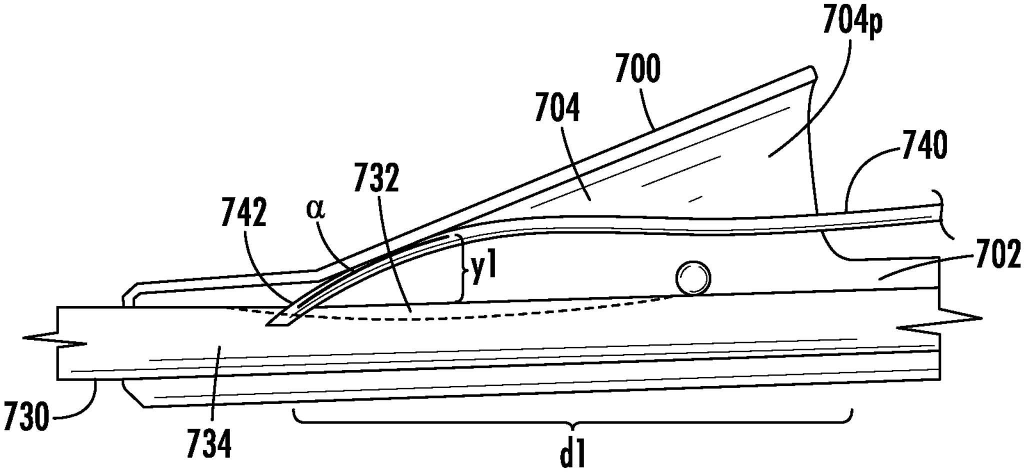
FIG. 7A illustrates a cross-sectional view of a guidewire being introduced into an aperture of a catheter through a port, according to an embodiment of the present disclosure.
Figure 7B:
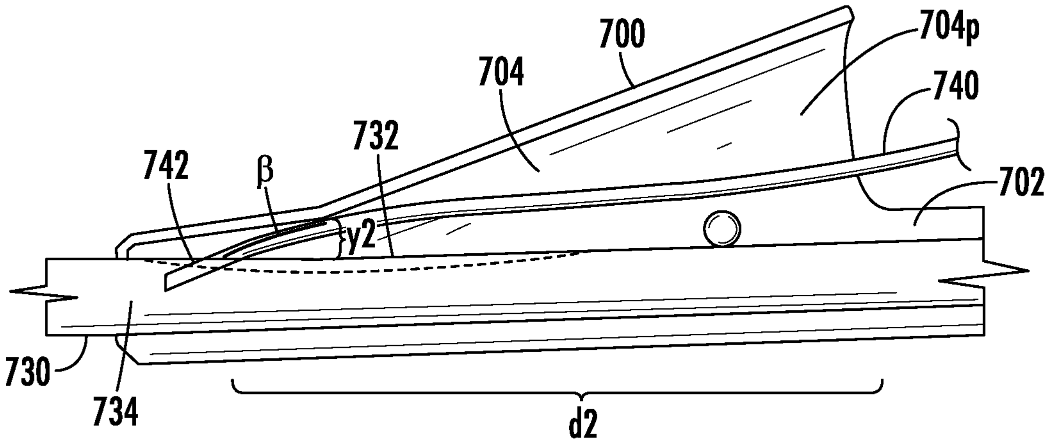
FIG. 7B illustrates a cross-sectional view of the guidewire being introduced into the aperture of the catheter through the port of FIG. 7A along a different location of the catheter.

Referring to FIGS. 7A and 7B, cross-sectional views of a guidewire 740 being introduced into an aperture 732 of a catheter 730 are illustrated, according to embodiments of the present disclosure. In FIG. 7A, the catheter 730 is extending through a main channel 702 of a port 700. The guidewire 740 is being introduced through an accessory channel 704 of the port 700 and into a lumen 734 of the catheter 730. The distal end 742 of the guidewire 740 is entering the aperture 732 at a first distance $d_1$ from a proximal end 704*p* of the accessory channel 704 and at a first height $y_1$ from the catheter 730. An angle $\alpha$ of the guidewire 740 entering the aperture 732 may not align axially with the lumen 734 of the catheter, causing failed access of guidewire 740 and prolonged setup of the guidewire and catheter for tool use. FIG. 7B illustrates the port 700 disposed along the catheter 730 more proximally than that of the arrangement in FIG. 7A. In FIG. 7B, the distal end 742 of the guidewire 740 is entering the aperture 732 at a distance $d_2$ from the proximal end 704*p* of the accessory channel 704 that is larger than the distance $d_1$ of FIG. 7A. Additionally, the first coincident point where the guidewire 740 contacts the accessory channel 704 proximal to its entry point through the aperture 732 is at a height $y_2$ that is smaller than the height $y_1$ of FIG. 7A. The larger second distance $d_2$ and smaller second height $y_2$ may allow the guidewire 740 room and/or constraint for a straighter, more aligned orientation within the lumen 734 with a straighter angle $\beta$ compared to the angle $\alpha$ of FIG. 7A (i.e., more axially aligned with itself). In various embodiments, a height $y_1$, $y_2$ may be about 0.1 inches to about 0.2 inches.

Figure 8A:
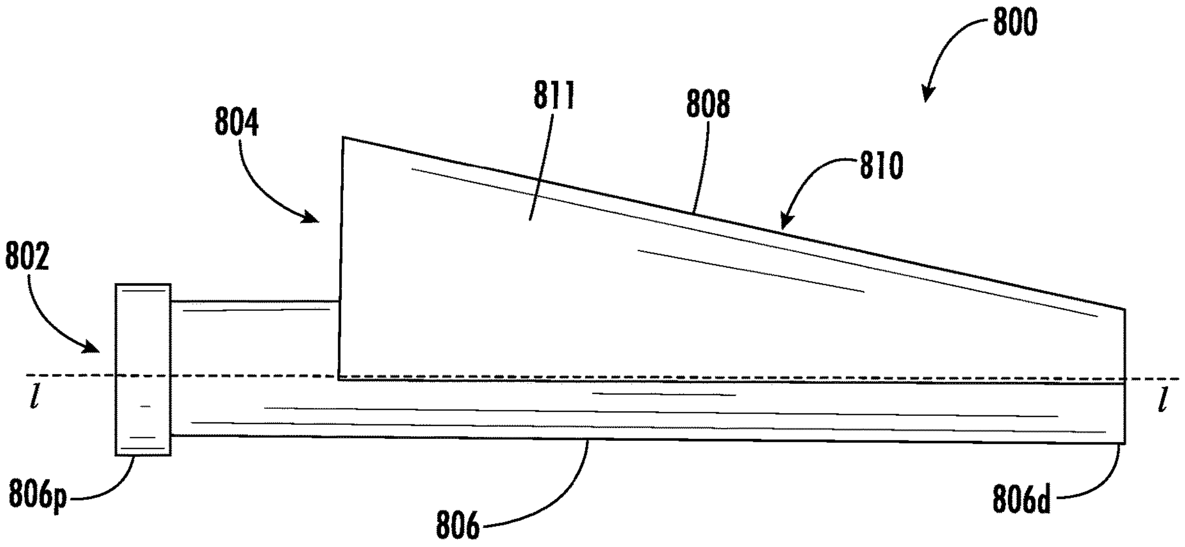
FIG. 8A illustrates a right view of a port, according to an embodiment of the disclosure.
Figure 8B:
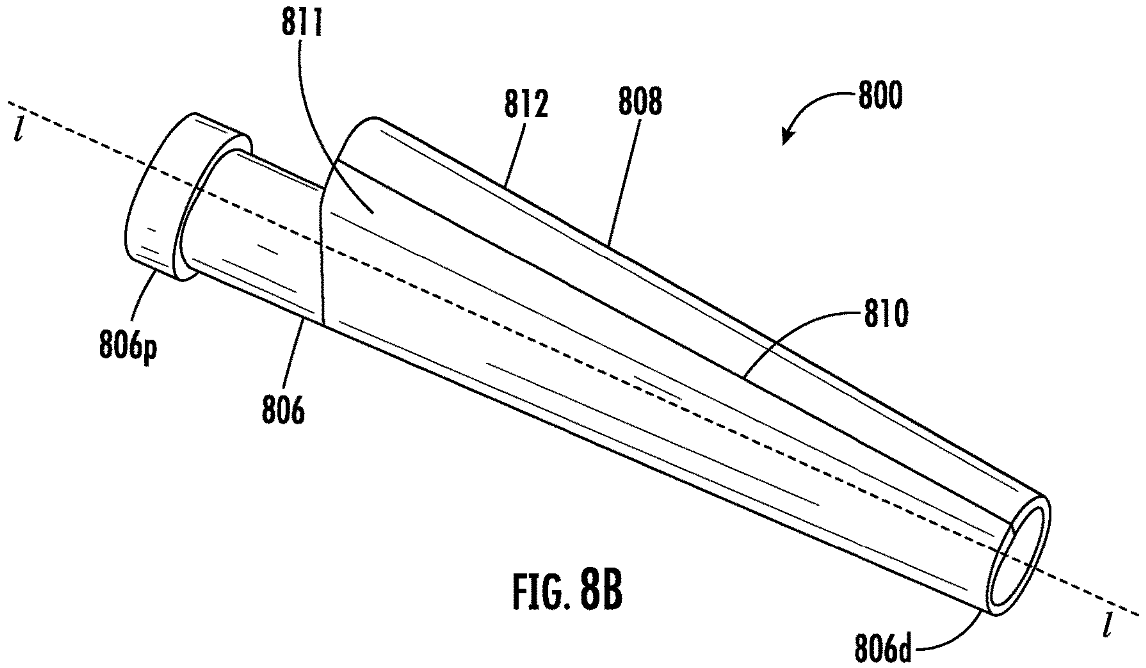
FIG. 8B illustrates a perspective view of the port of FIG. 8A.
Figure 8C:
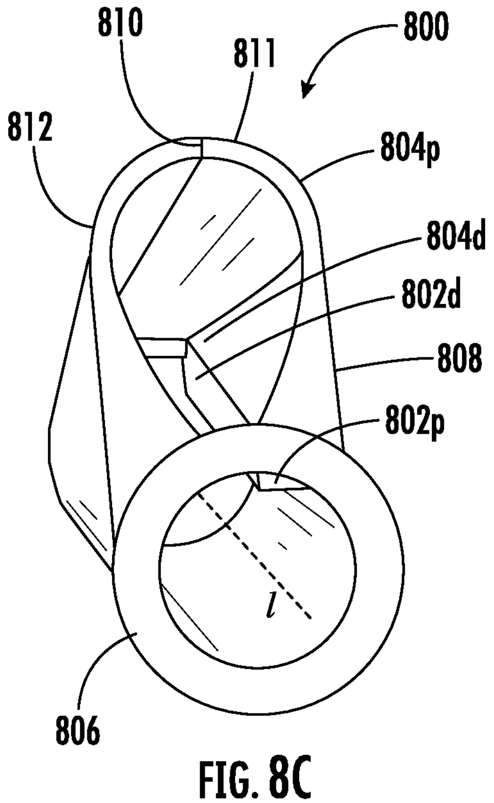
FIG. 8C illustrates a perspective view of the port of FIGS. 8A and 8B.

Referring to FIGS. 8A-8C, right and perspective views of a port 800 are illustrated, according to an embodiment of the disclosure. The port 800 includes a body 806 comprising a proximal end 806*p*, a distal end 806*d*, and a longitudinal axis $\ell$ extending therethrough. A main channel 802 extends along the longitudinal axis $\ell$ of the body 806 that is configured to be coaxial with a lumen of a catheter. The port 800 comprises an elastic material (e.g., compliant, capable of being manipulated with user hands to form, mount, exchange devices through, and/or the like such as a silicone, a rubber, a TPE, a urethane, a polymer, a combination thereof, or the like), such that various catheters of differing diameters may be disposed within the main channel 802, e.g., by manipulating an end 806*p*, 806*d* of the body 806 about a catheter. Another benefit of the elastic material construction of the port 800 is ease of assembly. For example, there is no need for glue/heat shrink to attach the port, unless desired. An extension 808 extends from the body 806. The extension 808 includes an accessory channel 804 extending through the extension 808. The accessory channel 804 is in fluid communication with the main channel 802 such that the accessory channel 804 may accept an accessory within it to guide the accessory towards accessing the main channel 802. The accessory channel 804 tapers to a smaller inner diameter towards the distal end 806*d* such that an accessory may have, e.g., an interference fit with the accessory channel 804. In various embodiments, the accessory channel 804 may include geometries, e.g., a positive stop disposed along the accessory channel 804, of embodiments described herein, such that an accessory is prevented from entering the main channel 802. The accessory lumen 804 includes a proximal portion 804*p* having a lateral width dimension wider than a remainder of the accessory lumen 804, e.g., that may assist with introducing an accessory into the accessory lumen 804. The main channel 802 includes a proximal shoulder 802*p* and a distal shoulder 802*d*. The shoulders 802*p*, 802*d* may be configured to abut ends of a radial aperture of a catheter extending through the main channel 802 as described herein. A slit 810 extends through the extension 808, through the accessory channel 804, and into the main channel 802 of the port 800. The slit 810 may be a rapid exchange feature as described herein, e.g., for moving a tool and/or an accessory therethrough. In various embodiments, the slit 810 may be one or more of an aperture, slot, channel, flap, perforation, weakened area, or the like along a length of the port 800. The extension 808 comprises a pair of guides 811, 812 disposed on opposing sides of the slit 810 about the longitudinal axis $\ell$. The pair of guides 811, 812 may be elastically manipulated, e.g., for accommodating, inserting, removing, or exchanging an accessory and/or a tool.

Figure 9A:
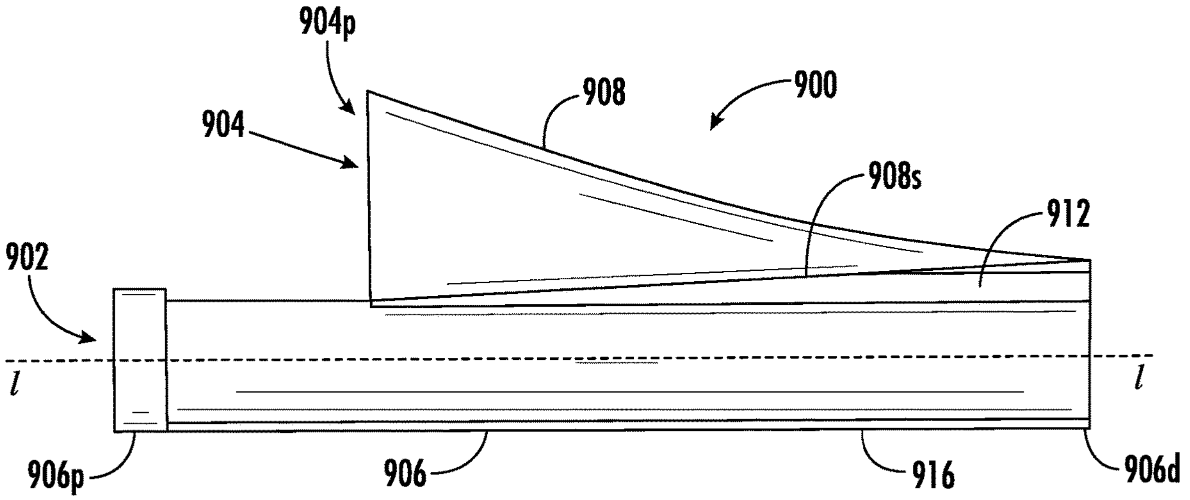
FIG. 9A illustrates a right view of a port, according to an embodiment of the disclosure.
Figure 9B:
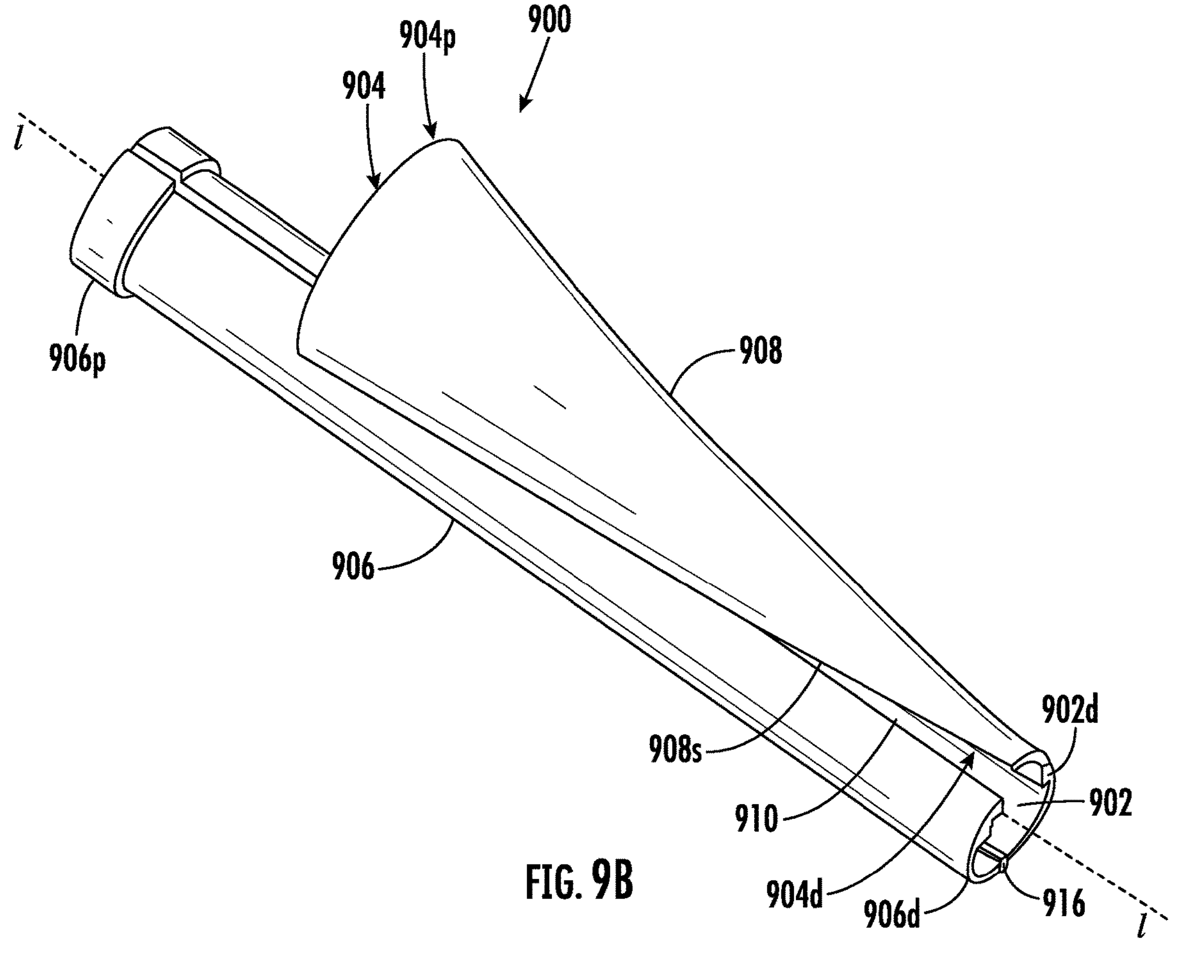
FIG. 9B illustrates a perspective view of the port of FIG. 9A.
Figure 9C:
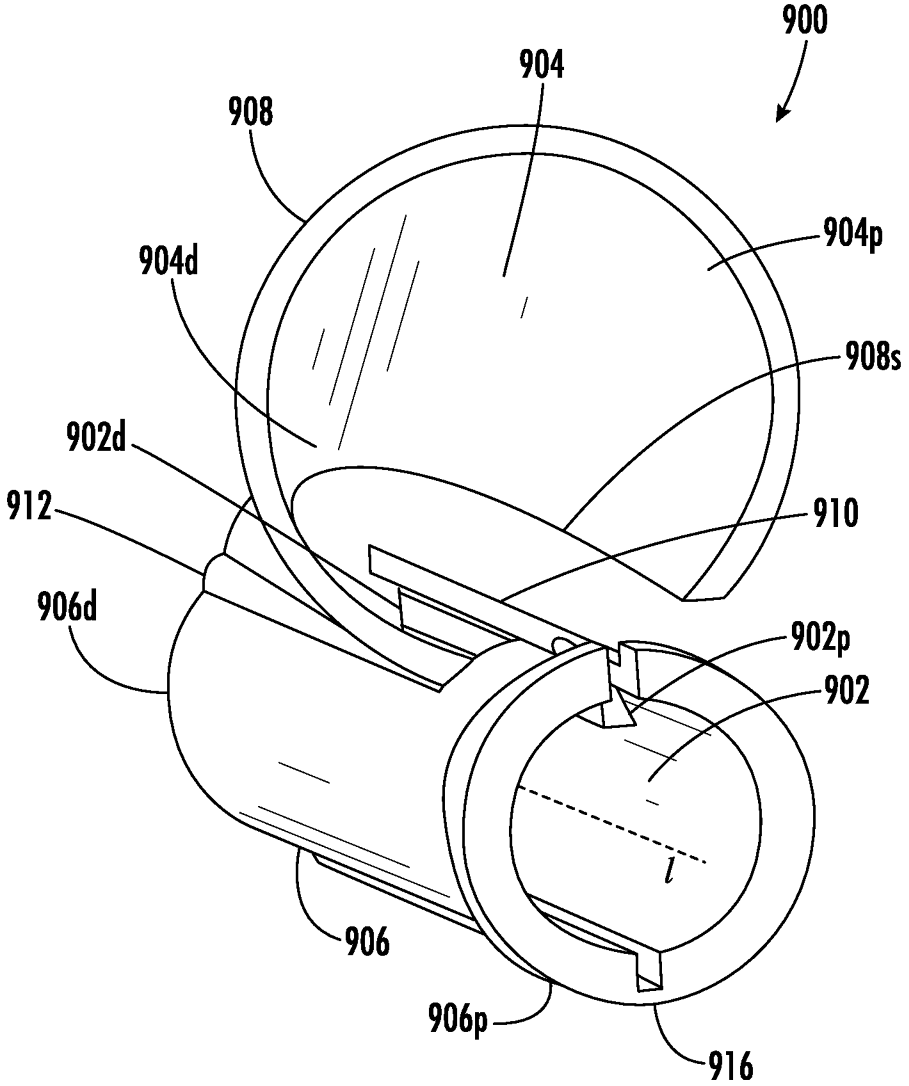
FIG. 9C illustrates a perspective view of the port of FIGS. 9A and 9B.

Referring to FIGS. 9A-9C, perspective and right views of a port 900 are illustrated, according to an embodiment of the disclosure. The port 900 includes a body 906 comprising a proximal end 906*p*, a distal end 906*d*, and a longitudinal axis $\ell$ extending therethrough. A main channel 902 extends along the longitudinal axis $\ell$ of the body 906 that is configured to be coaxial with a lumen of a catheter. The port 900 is illustrated in a closed configuration and is transitionable to an open configuration along a hinge 916 disposed along a thinned portion of a wall of the body 906. The port 900 may comprise an elastic material (e.g., compliant, capable of being manipulated with user hands to form, mount, exchange devices through, and/or the like such as a silicone, a rubber, a TPE, a urethane, a polymer, a combination thereof, or the like), beneficially a relatively hard elastic material, or an inelastic material, such that various catheters of differing diameters may be disposed within the main channel 902, e.g., by manipulating an end 906*p*, 906*d* of the body 906 about a catheter. An extension 908 extends from the body 906. The extension 908 is a flap forming a funnel-shape along the body 906 and defining an accessory channel 904. The flap of the extension 908 has a larger dimension of the funnel-shape at a proximal end 904*p* and a smaller dimension of the funnel-shape towards the distal end 904*d*. The extension 908 includes a slit 908*s* along a terminal end of the flap that extends laterally along the funnel-shape. The accessory channel 904 is in fluid communication with the main channel 902 such that the accessory channel 904 may accept an accessory within it to guide the accessory towards accessing the main channel 902. The funnel-shape of the accessory channel 904 tapers from a larger inner diameter at the proximal end 904*p* to a smaller inner diameter towards the distal end 904*d* such that an accessory may have an interference fit with the accessory channel 904. The proximal portion 904*p* has an inner diameter wider than a remainder of the accessory lumen 904, e.g., that may assist with introducing an accessory into the accessory lumen 904. In various embodiments, the accessory channel 904 may include geometries, e.g., a positive stop disposed along the accessory channel 904, of embodiments described herein, such that an accessory is prevented from entering the main channel 902. The main channel 902 includes a proximal shoulder 902*p* and a distal shoulder 902*d*. The shoulders 902*p*, 902*d* may be configured to abut ends of an aperture of a catheter extending through the main channel 902 as described herein. A slit 910 extends through the body 906 into the main channel 902 of the port 900. The slit 910 of the body 906, in combination with the slit 908*s* of the extension 908, may be a rapid exchange feature as described herein, e.g., for moving a tool and/or an accessory therethrough the slit 910 of the body 906 and the slit 908*s* of the extension 908. In various embodiments, the slits 910, 908*s* may be one or more of an aperture, slot, channel, flap, perforation, weakened area, or the like along a length of the port 900. The flap of the extension 908 may be elastically manipulated, e.g., for accommodating, inserting, removing, or exchanging an accessory and/or a tool, by moving the flap about a hinge 912 of the extension 908 that is a thinned portion along a wall of the extension 908. The hinge 912 extends along the extension 908 where the extension 908 is coupled to the body 906.

In various embodiments, a port may be coupled to a catheter by closing the port about a catheter along a hinge of the port. A port may be additionally or further coupled to a catheter by, e.g., application of a heat-shrink sleeve about a proximal and/or distal end of a body of the port and the catheter. A port may be additionally or further coupled to a catheter by manipulating the port over the catheter, forming an interference and/or friction fit. A port may be formed along a catheter during manufacturing of the catheter device. In various embodiments, a port material may include a lubricious additive and/or coating (e.g., a hydrophilic thermoplastic polyurethane elastomer, a cast nylon with a semi-crystalline material filled with oil lubricant, etc.) to assist with coupling the port to a catheter and/or for introducing an accessory or tool.

Embodiments of methods of introducing a tool into a catheter may include inserting an accessory into an accessory channel of a port. A distal portion of the accessory may interface and/or abut a portion of the accessory channel such as a positive stop so that the accessory stops and/or is held within the accessory channel and the tool may be advanced into a main channel of the port. The tool may be inserted through accessory and into a lumen of the catheter. The tool may be introduced into the accessory by a user or the tool may already be loaded at least partially into the accessory prior to introducing the accessory into the port. The tool may be laterally removed from the catheter through a rapid exchange feature of the catheter and/or the port. A second tool, catheter, or guidewire may be introduced into the catheter.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A catheter port for introducing an accessory, comprising:

a body comprising a proximal end, a distal end, a longitudinal axis extending therethrough, and a main channel extending along the longitudinal axis along a length of the body, wherein the main channel is substantially coaxial with a lumen of a catheter;

an extension extending from the body, the extension comprising an accessory channel extending through the extension, the accessory channel in fluid communication with the main channel, and the accessory channel configured to accept the accessory;

a positive stop disposed along the accessory channel, the positive stop configured to abut a distal end of the accessory; and a slit extending from the distal end of the body to the proximal end of the body, the slit extending through the extension and in fluid communication with the accessory channel;

wherein the extension comprises a pair of guides disposed on opposing sides of the slit along the body about the longitudinal axis;

wherein the body comprises a thinned portion along a wall of the main channel, the thinned portion disposed along the length of the body opposing the slit such that the body and the pair of guides comprise an open configuration wherein the pair of guides are positioned away from each other about the thinned portion and a closed position wherein the pair of guides are positioned towards each other about the thinned portion.

2. The catheter port of claim 1, wherein the slit is configured to receive a tool laterally removable from the main channel through the slit and out of the catheter port.

3. The catheter port of claim 1, wherein the accessory channel comprises a larger lateral width dimension at a proximal portion that is smaller than a lateral width dimension at a distal portion.

4. The catheter port of claim 1, wherein a proximal end of the accessory channel comprises a funnel-shape having a maximum lateral width dimension that is larger than the remainder of the accessory channel.

5. The catheter port of claim 1, wherein the main channel further comprises at least one of a distal shoulder configured to abut a distal end of an aperture of the catheter and a proximal shoulder configured to abut a proximal end of the aperture of the catheter.

6. The catheter port of claim 1, wherein the positive stop comprises an annular aperture having a diameter that abuts an outer diameter of the accessory and is large enough to accept a diameter of a tool disposed within the accessory.

7. The catheter port of claim 1, wherein the extension comprises at least one concave portion along an outer surface of the extension.

8. The catheter port of claim 1, wherein the extension comprises a flap forming a funnel-shape extending along and laterally from the body, the flap having a larger lateral width dimension of the funnel-shape towards the proximal end than a lateral width dimension of the funnel-shape towards the distal end, and wherein the slit is disposed along a terminal proximal end of the flap and laterally along the funnel-shape.

9. The catheter port of claim 1, wherein a proximal end of the accessory channel comprises a funnel-shape having a maximum lateral width dimension that is larger than the remainder of the accessory channel, wherein a midportion of the accessory channel has a diameter smaller than a proximal portion, and wherein the positive stop has a diameter smaller than the midportion.

10. A catheter port for introducing an accessory, comprising:

a body comprising a proximal end, a distal end, a longitudinal axis extending therethrough, and a main channel extending along the longitudinal axis along a length of the body, wherein the main channel is substantially coaxial with a lumen of a catheter;

an extension extending from the body, the extension comprising an accessory channel extending through the extension, the accessory channel in fluid communication with the main channel, and the accessory channel configured to accept the accessory;

a positive stop disposed along the accessory channel, the positive stop configured to abut a distal end of the accessory; and a slit extending from the distal end of the body to the proximal end of the body, the slit extending through the extension and in fluid communication with the accessory channel;

wherein the extension comprises a flap forming a funnel-shape extending along and laterally from the body, the flap having a larger lateral width dimension of the funnel-shape towards the proximal end than a lateral width dimension of the funnel-shape towards the distal end, wherein the slit is disposed along a terminal proximal end of the flap and laterally along the funnel-shape, and wherein the flap further comprises a thinned portion along a wall of the flap, the thinned portion extending along the flap where the flap extends laterally from the body.

11. A catheter port for introducing an accessory, comprising:

a body comprising a proximal end, a distal end, a longitudinal axis extending therethrough, and a main channel extending along the longitudinal axis along a length of the body, wherein the main channel is substantially coaxial with a lumen of a catheter;

an extension extending from the body, the extension comprising an accessory channel extending through the extension, the accessory channel in fluid communication with the main channel, and the accessory channel configured to accept the accessory;

a positive stop disposed along the accessory channel, the positive stop configured to abut a distal end of the accessory; and a slit extending from the distal end of the body to the proximal end of the body, the slit extending through the extension and in fluid communication with the accessory channel;

wherein the catheter port comprises an open configuration in which the body and extension are opened along a hinge in the form of a thinned portion extending along the body parallel with the longitudinal axis, and a closed configuration in which the body and extension are closed along the hinge such that the main channel, the accessory channel, and the slit are formed.

12. The catheter port of claim 11, wherein the extension comprises a pair of guides disposed on opposing sides of the slit along the body about the longitudinal axis.

13. The catheter port of claim 11, wherein the accessory channel comprises a larger lateral width dimension at a proximal portion that is smaller than a lateral width dimension at a distal portion.

14. The catheter port of claim 11, wherein the extension comprises a flap forming a funnel-shape extending along and laterally from the body, the flap having a larger lateral width dimension of the funnel-shape towards the proximal end than a lateral width dimension of the funnel-shape towards the distal end, and wherein the slit is disposed along a terminal proximal end of the flap and laterally along the funnel-shape.

15. A catheter system, comprising:

a catheter port in accordance with claim 11;

the catheter disposed through the main channel of the port; and the accessory insertable within the accessory channel such that the accessory abuts the positive stop.

16. The catheter system of claim 15, wherein the main channel further comprises a shoulder configured to extend into a lumen of the catheter such that the shoulder abuts an end of a radial aperture of the catheter.

17. The catheter system of claim 15, wherein the extension comprises a flap forming a funnel-shape extending along and laterally from the length of the body with a larger lateral width dimension of the funnel towards the proximal end than a lateral width dimension of the funnel towards the distal end.

18. The catheter system of claim 15, wherein a proximal end of the accessory channel comprises a funnel-shape having a maximum lateral width dimension that is larger than the remainder of the accessory channel, wherein a midportion of the accessory channel has a diameter smaller than a proximal portion, and wherein the positive stop has a diameter smaller than the midportion.

19. The catheter port of claim 11, wherein a proximal end of the accessory channel comprises a funnel-shape having a maximum lateral width dimension that is larger than the remainder of the accessory channel, wherein a midportion of the accessory channel has a diameter smaller than a proximal portion, and wherein the positive stop has a diameter smaller than the midportion.

20. The catheter port of claim 11, wherein the catheter port further comprises a protrusion and an aperture, and wherein the protrusion is configured to engage with the aperture when the port is transitioned from the open configuration to the closed configuration.

* * * * *